(12) United States Patent
Widdershoven

(10) Patent No.: US 8,673,772 B2
(45) Date of Patent: Mar. 18, 2014

(54) BIOSENSOR CHIP AND A METHOD OF MANUFACTURING THE SAME

(75) Inventor: Frans Widdershoven, Eindhoven (NL)

(73) Assignee: NXP B.V., Eindhoven (NL)

( * ) Notice: Subject to any disclaimer, the term of this patent is extended or adjusted under 35 U.S.C. 154(b) by 102 days.

(21) Appl. No.: 13/371,627

(22) Filed: Feb. 13, 2012

(65) Prior Publication Data

US 2013/0207204 A1  Aug. 15, 2013

(30) Foreign Application Priority Data

Feb. 28, 2011 (EP) .................................. 11156247

(51) Int. Cl.
*H01L 21/00* (2006.01)

(52) U.S. Cl.
USPC ........... 438/638; 438/627; 438/629; 438/631; 438/643; 438/645; 257/750; 257/758; 257/773; 257/774; 257/776

(58) Field of Classification Search
USPC ................. 438/638, 627, 629, 631, 643, 645; 257/750, 758, 773, 774, 776, E21.579, 257/E21.58, E21.585
See application file for complete search history.

(56) References Cited

U.S. PATENT DOCUMENTS

| | | | | |
|---|---|---|---|---|
| 6,376,353 B1* | 4/2002 | Zhou et al. | ...... | 438/612 |
| 6,677,226 B1* | 1/2004 | Bowen et al. | ...... | 438/601 |
| 7,242,102 B2* | 7/2007 | Kang et al. | ...... | 257/786 |
| 7,348,671 B2* | 3/2008 | Kirby | ...... | 257/753 |
| 7,514,354 B2* | 4/2009 | Park et al. | ...... | 438/629 |
| 7,648,900 B2* | 1/2010 | Kirby | ...... | 438/612 |
| 8,067,249 B2* | 11/2011 | Frey et al. | ...... | 438/1 |
| 8,470,191 B2* | 6/2013 | Mayer et al. | ...... | 216/92 |
| 2002/0006717 A1* | 1/2002 | Yamaha | ...... | 438/612 |
| 2003/0003703 A1* | 1/2003 | Barth et al. | ...... | 438/601 |
| 2003/0203614 A1* | 10/2003 | Rajagopalan et al. | ...... | 438/622 |
| 2004/0245637 A1* | 12/2004 | Horak et al. | ...... | 257/758 |
| 2006/0166498 A1* | 7/2006 | Kirby | ...... | 438/667 |
| 2007/0069334 A1* | 3/2007 | Beach et al. | ...... | 257/536 |
| 2007/0071052 A1* | 3/2007 | Hommel et al. | ...... | 372/46.012 |
| 2008/0119043 A1* | 5/2008 | Kirby | ...... | 438/643 |
| 2008/0173976 A1* | 7/2008 | Stamper et al. | ...... | 257/531 |
| 2008/0272460 A1* | 11/2008 | Beach et al. | ...... | 257/536 |
| 2008/0293233 A1* | 11/2008 | Chinthakindi et al. | ...... | 438/612 |

FOREIGN PATENT DOCUMENTS

| WO | 2005/106478 A1 | 11/2005 |
|---|---|---|
| WO | 2008/132656 A2 | 11/2008 |
| WO | 2009/122314 A1 | 10/2009 |

OTHER PUBLICATIONS

Eversmann, Bjorn et al. "A 128×128 CMOS Biosensor Array for Extracellular Recording of Neural Activity", IEEE Journal of Solid-State Circuits, vol. 38, No. 12, pp. 2306-2317 (2003).

(Continued)

*Primary Examiner* — Julio J Maldonado
*Assistant Examiner* — Jaehwan Oh

(57) ABSTRACT

A method of forming a biosensor chip enables a bond pad and detector electrode to be formed of different materials (one is formed of a connection layer such as copper and the other is formed of a diffusion barrier layer such as tantalum or tantalum nitride). A single planarizing operation is used for both the bond pad and the detector electrode. By using the same processing, resist patterning on an already-planarized surface is avoided, and the cleanliness of both the bond pad and detector electrode is ensured. Self-aligned nanoelectrodes and bond pads are obtained.

15 Claims, 5 Drawing Sheets

(56) References Cited

OTHER PUBLICATIONS

Martin, Steven M. et al. "Design, Implementation, and Verification of a CMOS-Integrated Chemical Sensor System", Proceeding of the 2004 International Conference on MEMS, NANO and Smart Systems (ICMENS'04), pp. 7 (2004).

Thewes, Roland et al. "A CMOS Medium Density DNA Microarray with Electronic Readout", Materials Research Society Symposium Proceedings, vol. 869, pp. D3.4.1-D3.4.11 (2005).

Extended European Search Report for EP Patent Appln. No. 11156247.6 (Aug. 17, 2011).

* cited by examiner

BIOSENSOR CHIP AND A METHOD OF MANUFACTURING THE SAME

CROSS-REFERENCE TO RELATED APPLICATIONS

This application claims the priority under 35 U.S.C. §119 of European patent application no. 11156247.6, filed on Feb. 28, 2011, the contents of which are incorporated by reference herein.

The invention relates to a biosensor chip. Moreover, the invention relates to a method of manufacturing a biosensor chip.

A biosensor may be denoted as a device that may be used for the detection of an analyte that combines a biological component with a physicochemical or physical detector component.

For instance, a biosensor may be based on the phenomenon that capture molecules immobilized on a surface of a biosensor may selectively hybridize with target molecules in a fluidic sample, for instance when an antibody-binding fragment of an antibody or the sequence of a DNA single strand as a capture molecule fits to a corresponding sequence or structure of a target molecule. When such hybridization or sensor events occur at the sensor surface, this may change the electrical properties of the surface, which electrical properties may be detected as the sensor event.

WO 2005/106478 discloses a method for functionalizing biosensors, particularly those based on semiconductor chips mounted on a finished processed wafer, provided with sensor fields placed thereupon, which may be arranged in an array, and for carrying out a functionalization, for example, with organic molecules such as nucleic acids like DNA, RNA and PNA or with their derivatives, proteins, sugar molecules or antibodies.

WO 2008/132656 discloses a biosensor in which the sensor active region is formed as part of the back-end processing of the semiconductor wafer used to form the biosensor chip. The back-end processing includes contacts, insulators, metal levels, and bonding sites for chip-to-package connections. These layers are generally out of direct contact with the processed semiconductor substrate. The front-end processing relates to processing of an integrated circuit where the individual devices (transistors, resistors, etc.) are patterned in the semiconductor, and generally covers everything up to (but not including) the deposition of metal layers.

This invention relates particularly to the back-end processing steps used to form the sensor electrodes and also the bond pads used to make electrical contact down to the underlying devices formed in the preceding front-end processing steps.

A known current capacitive biosensor chip uses polished copper-filled vias as nanoelectrodes. However, copper is easily corroded during storage, post-processing or detection steps. Therefore nanoelectrodes made of an alternative corrosion-resistant metallic material would be preferred. However, the combination of different materials for different electrical contacts complicates the processing. For example, the nanoelectrode material should be self-aligned to the via holes to be able to make nanoelectrodes with the required small circular diameter at the chip surface.

According to the invention, there is provided a method of forming a biosensor chip, comprising:

forming semiconductor components in a semiconductor wafer;

forming filled electrically conductive connection regions in a dielectric layer overlying the semiconductor components, the filled electrically conductive connection regions making electrical contact to the semiconductor components, and comprising at least a bond pad connection region and a detection electrode connection region;

forming a first capping layer over the dielectric layer, and forming at least one filled electrically conductive connection region in the first capping layer making contact with the detection electrode connection region, wherein no connection regions are formed over the at least one bond pad connection region;

forming a second capping layer over the first capping layer;

forming at least one via in the second capping layer, aligned with the at least one filled electrically conductive connection region in the first capping layer;

forming a bond pad opening in the second capping layer, over the bond pad connection region and extending down to the dielectric layer;

forming a diffusion barrier over the top of the structure and which completely fills the at least one via in the second capping layer;

providing a bond pad connection layer over the top of the structure and which fills the diffusion barrier-lined bond pad opening; and planarizing the structure down to the second capping layer.

This method enables a bond pad and detector electrode to be formed of different materials (one is formed of the connection layer such as copper and the other is formed of the diffusion barrier layer such as tantalum nitride). A single surface treatment operation (the planarizing) is used for both the bond pad and the detector electrode. By using the same processing, resist patterning on an already-planarized surface is avoided, and the cleanliness of both the bond pad and detector electrode is ensured. The planarizing step causes the patterning of the bond pad and detector electrode. By removing material down to the second capping layer, the detector electrodes and bond pad is automatically aligned with the previous detector electrode region and bond pad opening, so that the final bond pad and detector electrode can be considered to be self-aligned, in that no photolithographic process is used to determine the shape and position of the bond pad and detector electrode. This means that the need to provide overlay tolerances when defining the bond pad and detector electrode shape is avoided.

The bond pad opening is defined through both capping layers so that the depth is greater than the via depth for the detector electrodes. In this way, the bond pad opening is not completely filled by the diffusion barrier layer.

The same mask can be used for forming the at least one filled electrically conductive connection via in the first capping layer and for forming the at least one via in the second capping layer.

Forming the first capping layer can further comprise forming an etch stop layer beneath the first capping layer and forming the second capping layer further comprises forming an etch stop layer beneath the second capping layer. These are used to stop the etching of the detector electrode via and the bond pad opening.

Forming the diffusion barrier can comprise forming a tantalum nitride layer which completely fills the at least one via in the second capping layer, and a tantalum layer over the tantalum nitride layer, wherein the tantalum nitride layer is thicker than the tantalum layer.

In this way, the detector electrode regions are filled with a tantalum nitride diffusion barrier stack with a tantalum nitride layer that is thick enough to completely fill the via holes. The much wider and deeper bond pad opening is only filled partially by the tantalum nitride/tantalum diffusion barrier.

The planarizing removes the bond pad connection layer, the tantalum layer, and the excess tantalum nitride from the detection electrode area, so that only tantalum nitride remains in the detector electrode via, filling it up to surface of the second capping layer.

The (or each) etch stop layer can comprise silicon nitride, the first and second capping layers can comprise silicon oxide layers or combinations of silicon oxide and silicon nitride layers.

The filled electrically conductive connection regions in the dielectric layer and the filled electrically conductive connection region in the first capping layer can be each filled with copper.

The bond pad connection layer also preferably comprises copper. For this purpose, a copper seed layer can be deposited, and copper can be electroplated. A copper chemical mechanical polishing process can be used to planarize the copper in the bond pad opening, and to remove the Tantalum nitride/Ta barrier at the chip surface. This leaves planarized tantalum nitride plugs in the detector electrode vias. These tantalum nitride plugs constitute the nanoelectrodes of the biosensor. A thin native tantalum oxide will form on top of the tantalum nitride surface. This protects the surface from corrosion. Biological probe molecules, needed to provide the required specificity of the biosensor, can easily be attached to the tantalum oxide layer. The copper bond pads can be protected against corrosion with regular corrosion inhibitors like BTA, or with a thiol-based self-assembled monolayer. Electrical connections can be made to the bond pads with aluminium bond wires.

The invention also provides a biosensor chip, comprising:
 semiconductor components formed in a semiconductor wafer;
 filled electrically conductive connection regions in a dielectric layer overlying the semiconductor components, the filled electrically conductive connection regions making electrical contact to the semiconductor components, and comprising at least a bond pad connection region and a detection electrode connection region;
 a first capping layer over the dielectric layer having at least one filled electrically conductive connection via in the first capping layer making contact with the detection electrode connection region;
 a second capping layer over the first capping layer and having at least one via aligned with the at least one filled electrically conductive connection via in the first capping layer and a bond pad opening over the bond pad connection region and extending down to the dielectric layer;
 wherein the bond pad opening is lined with a diffusion barrier comprising a tantalum nitride layer and a tantalum layer over the tantalum nitride layer and is filled over the diffusion barrier with a conductor, wherein the tantalum nitride layer is thicker than the tantalum layer, and wherein the at least one via of the second capping layer is completely filled with tantalum nitride.

An example of the invention will now be described in detail with reference to the accompanying drawings, in which:

FIG. 1 is taken from WO2008/132656 and is used to explain the type of biosensor chip to which the invention can be applied.

Figure 1:
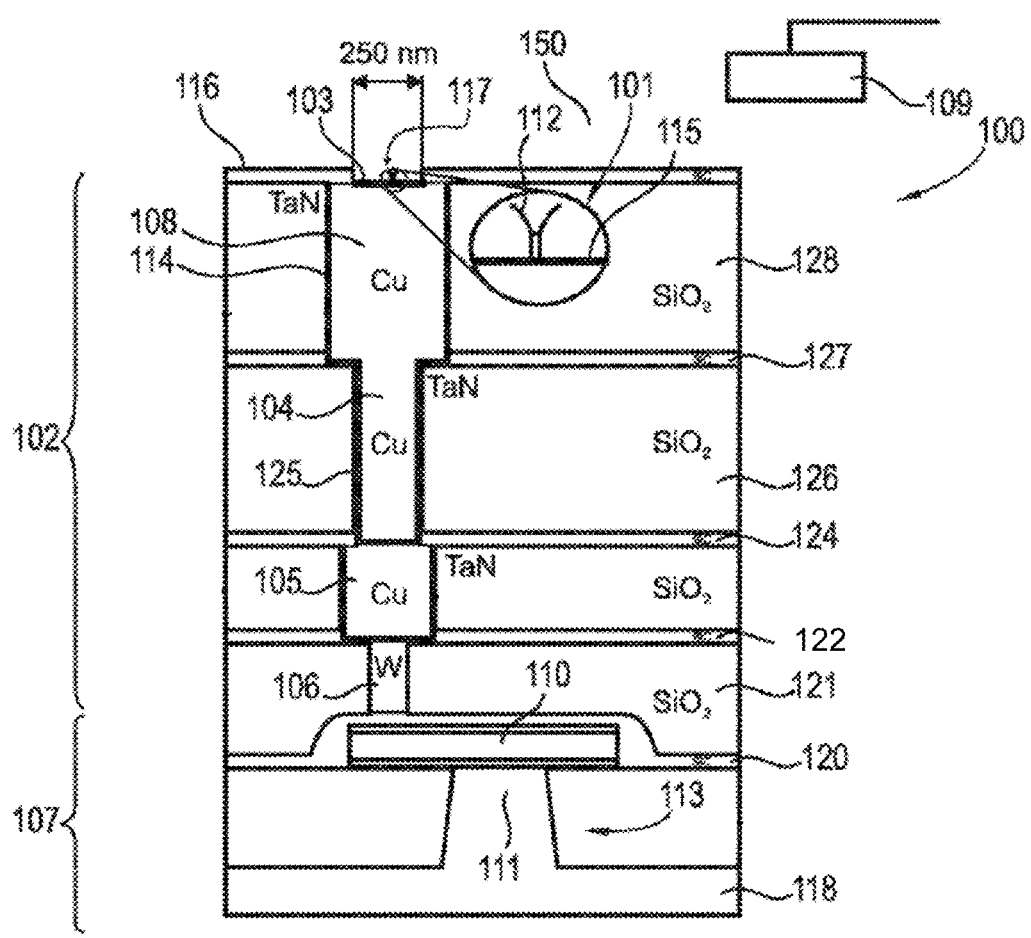
FIG. 1 shows a known biosensor design.

The biosensor chip 100 is adapted for detecting biological particles (such as antigens, not shown in the figure) and comprises a sensor active region 101 being sensitive for the biological particles and being arranged on top of a back end processing part 102 of the biosensor chip 100. More particularly, the sensor active region 101 is arranged at an upper surface 103 of the region 102 of the biosensor chip 100.

A plurality of intermediate metallization structures 104 to 106 formed as part of the back end processing part 102 are provided so that the sensor active region 101 is electrically coupled to a front end processing part 107 of the biosensor chip 100 via the plurality of intermediate metallization structures 104 to 106.

More particularly, a nanoelectrode 108 forming part of the sensor active region 101 is electrically coupled via the plurality of intermediate metallization structures 104 to 106 to a field effect transistor 113 integrated in the part 107.

A capacitor structure is partially formed in the back end part 102 and is arranged such that a capacitance value of the capacitor is influenced by a detection event at the sensor active region 101 (that is by a binding of antigens (not shown) to an antibody 112 immobilized on the surface 103 of the sensor active region 101), since such a detection event may have an impact on the value of the permittivity in a sensor pocket 117. More particularly, a first electrode of such a capacitor is formed by the copper layer 108, and a second electrode of this capacitor is formed by an electrolyte 150, connected by a counter electrode 109 which is, in the present embodiment, provided apart from the monolithically integrated layer sequence 100. Alternatively, it is possible to integrate an electrically conductive structure forming the second electrode of the capacitor in the layer stack.

More particularly, the actual capacitor in the biosensor 100 is an electrolytic capacitor. The sensor 100 in this case is immersed in an electrolyte 150 during the measurement. The electrolyte 150 can be the analyte itself or another conducting fluid that replaces the analyte after capturing of the antigens by the immobilized capture probes 112 on the SAM surface. The copper nanoelectrode 108 is one capacitor plate, the conducting fluid 150 is the other capacitor plate. The two plates 108, 150 are separated by the self-assembled monolayer (SAM) 115, which acts as the dielectric of the capacitor. When bio-molecules are attached to the SAM 115 (for instance as a result of the immobilization of the capture probes 112 on the SAM surface 115) or captured by the capture probes 112 (for instance as a result of the capturing of antigens by the capture probes 112) the dielectric properties of the capacitor's dielectric will change, and consequently also the capacitance of the capacitor. The electrolyte 150 is connected with the counter electrode 109.

As schematically indicated in FIG. 1, the transistor structure 113 is formed in the front end part 107 and is electrically coupled to the sensor active region 101 via the plurality of metallization structures 104 to 106, 108. A gate region 110 of such a transistor 113 is shown, as well as a channel region 111. Source/drain regions are located in front of and behind the plane of the drawing, respectively, and therefore are not indicated explicitly in FIG. 1. They may be formed as doped regions electrically coupled to both sides of the channel region 111, as known by the skilled person.

In this example the copper plug 105 is formed in a first metallization layer, the filled copper via 104 is formed in a first via formation process (via mask 1), the copper plug 108 is formed in a second metallization layer, and the sensor pocket depression 117 is formed in a second via formation process (via mask 2).

There may be other circuit components integrated with the transistor. Generally, these are referred to as semiconductor components in this application. This invention is not concerned with the transistor design or the circuit of which the transistor forms a part. Accordingly no further description is given.

As shown in FIG. 1, at least one antibody molecule 112 is immobilized at a surface 103 of the sensor active region 101 and is adapted for interacting with biological particles. Particularly, the antibody 112 is adapted for interacting with a corresponding antigen. The copper metallization structure 108 may have, at the surface 103, a dimension of 250 nm and therefore forms a nanoelectrode at which a detection event may take place. The nanoelectrode 108 is formed of copper material lined with a tantalum nitride layer 114. As can further be taken from FIG. 1, a SAM layer 115 (self assembled monolayer) is bridging the copper structure 108 and the antibody 112. The bare copper surface that remains after the final chemical mechanical polishing (CMP) step may oxidize rapidly in air or water. Therefore usually BTA (a corrosion inhibitor) is deposited during this CMP step (or during the subsequent cleaning step, or after the opening of the recess 117 in electrically insulating layer 116) to suppress this oxidation. In this way the wafers can be stored for some time (several days or perhaps even weeks) before the SAM 112 is deposited. Just before the SAM deposition, the BTA is removed from the copper surface.

Experimentally it is found that some wet-chemical SAM deposition recipes actually remove BTA themselves. In that case it is not strictly necessary to remove the BTA before the SAM deposition because it will happen automatically. After the SAM deposition it is not possible to deposit BTA anymore because the BTA would contaminate the SAM surface. Instead, a proper SAM should act as a corrosion inhibitor by itself. Alternatively, the sensor chips can be stored in a non-oxidizing atmosphere after the SAM deposition.

The biosensor chip 100 comprises an electrically insulating layer 116 forming part of the top surface of the biosensor chip 100 and having a recess 117, wherein an exposed surface 103 of the sensor active region 101 is provided as a sensing pocket volume in the recess 117.

The biosensor chip 100 is manufactured in CMOS technology, starting from a silicon substrate 118, the surface of which is shown in FIG. 1, and which may have a P well or an N well. Bond pads for electrically contacting the biosensor chip 100 may be provided but are not shown in FIG. 1. The CMOS processing uses dielectric layers 121, 123, 126, 128, typically oxide layers and etch stop layers 120, 122, 124, 127.

The bond pads are typically manufactured using the same process steps as for the sensor electrodes.

Figure 2:
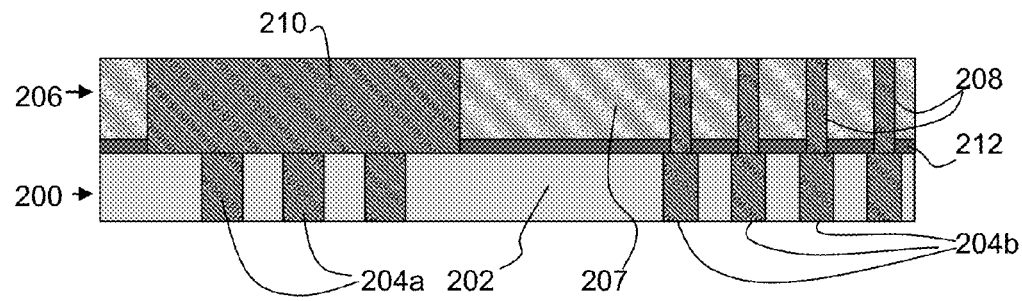
FIG. 2 shows how bond pads and detector electrodes are conventionally arranged in an embodiment described in WO2008/132656.

FIG. 2 shows the top layers of a known biosensor structure which forms bond pads as well as a plurality of detector nanoelectrodes.

At present, an array of 256×256 nanoelectrodes is known and has been commercialized, but much larger arrays of nanoelectrodes are expected in future.

As explained above, semiconductor wafers are processed with the standard CMOS flow up to and including the top metal layer (which can be the level 2 metal as in FIG. 1, or it can be a higher metal level such as the level 4 metal in a different sensor structure).

FIG. 2 shows the top metal layer 200 in the CMOS structure, which is the metal layer used to form the nanoelectrodes. Thus, the layer 200 can be considered to correspond to the layer 114, 128 in FIG. 1. In alternative implementations, the structure beneath the nanoelectrodes can be different, with a different arrangement of metallization layers and via masks. For example the top metal layer can be the level 4 metal layer.

The top layer comprises a low dielectric constant oxide layer 202, such as carbon-doped SiO2, with metal 2 copper grids 204a and islands 204b. The grids 204a are provided for making the bond pad connections to the integrated circuit components beneath. The bond pad is provided as a read out terminal for example, and/or for power or clock supply to the chip. The islands 204b are provided for making the detection signal connection to the transistor beneath.

A top layer 206 comprises an oxide capping layer 207, such as SiO2, with copper inserts 208 to form the nanoelectrodes, but also a copper bond pad 210.

The additional biosensor-specific processing, above the top metal layer 200 of the CMOS process, consists of:

(i) Deposition of a silicon nitride (SiN) etch stop layer 212 and the oxide cap layer 207.

(ii) Patterning of the nanoelectrode holes for the nanoelectrodes 208, e.g. with the Via 4 mask of the CMOS process;

(iii) Patterning of the bond pad holes with a further "pad open" mask;

(iv) Deposition of a tantalum nitride/tantalum diffusion barrier layer (not shown) and a thick copper (Cu) layer;

(v) Copper CMP (chemical mechanical polishing) and removal of tantalum nitride/tantalum diffusion barrier from the top surface. This results in the structure shown in FIG. 2.

In this process, copper nanoelectrodes and copper bond pads are polished by the same process.

Figure 3:
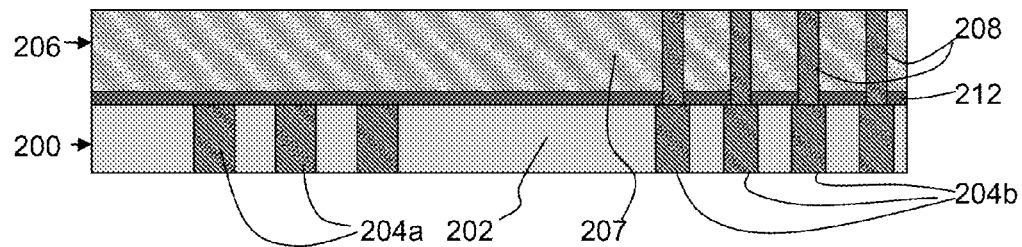
FIGS. 3 to 9 show sequential steps in an example of method of the invention to form a biosensor of the invention.

FIG. 3 shows the first step in an example of the process flow in accordance with the invention, and which achieves self-aligned tantalum nitride nanoelectrodes and copper bond pads.

Tantalum nitride (TaN) nanoelectrode surfaces have much better corrosion resistance than copper. The resulting functionalized nanoelectrodes have superior overall stability compared to conventional copper- or gold-based nanoelectrodes (functionalized with intermediate thiol-based SAMs).

In advanced CMOS processes, a TaN layer is used for adhesion to the dielectric layers (e.g. 202 and 207), and to avoid copper diffusion along grain boundaries in the diffusion barrier. The Ta is used because it does not mix with copper. Thus, the combination of TaN and Ta is used in standard advanced CMOS processes. The invention makes use of these existing materials used in CMOS processes to enable integration of the additional biosensor processing into a standard advanced CMOS process. Because Ta alone does not adhere well to the dielectric layers, it is less suitable for use as a bond pad.

The process starts with a modification of the default flow, where the patterning of the copper bond pads is skipped. As shown in FIG. 3, nanoelectrodes 208 are formed in the same manner as shown in FIG. 2, with the nanoelectrode openings formed with the standard via mask (e.g. Via mask 4) for example, but no patterning of the cap layer 206 (which comprises the dielectric 207 and metal plugs 208) is provided in the region where the bond pad is to be formed.

The original polished copper nanoelectrodes now serve as interconnection vias for subsequent tantalum nitride nanoelectrodes as explained below.

Figure 4:
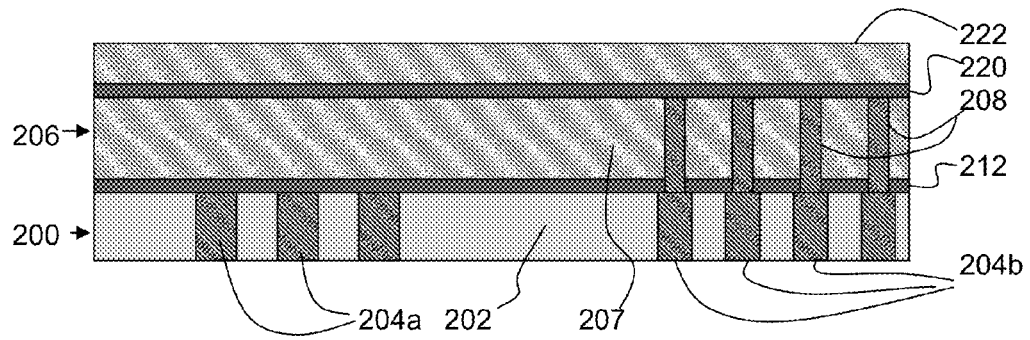

As shown in FIG. 4, a second SiN etch stop layer 220 and a thinner oxide cap layer 222 are deposited. The total thickness of these two layers should be comparable to the width of the subsequent nanoelectrode holes (shown in FIG. 5), so that the aspect ratio (depth:width) of these holes is less than 1.5, and even more preferably less than 1, to avoid problems with tantalum nitride filling.

A silicon nitride layer (not shown) may be deposited on top of the thin oxide layer 222. This combination is easier to pattern.

Figure 5:
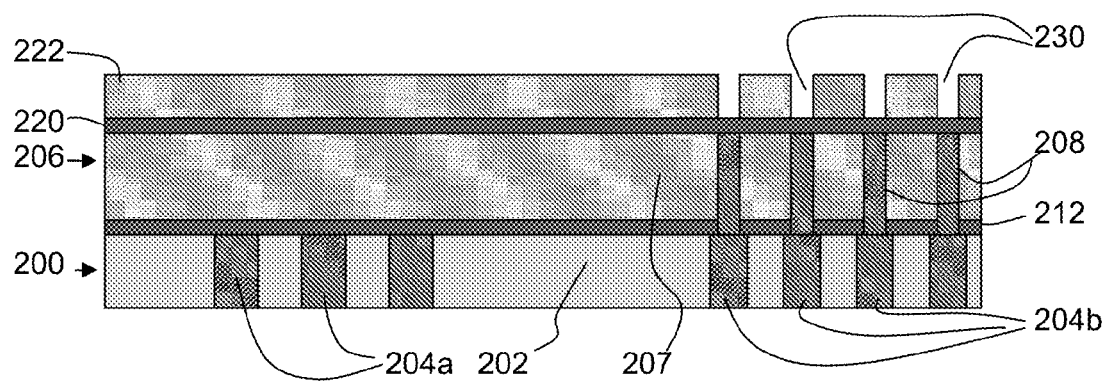

Shallow nanoelectrode holes 230 are patterned in the top dielectric layer 222 with the same mask used to form the original nanoelectrodes 208 of FIG. 3 (the Via 4 mask), as shown in FIG. 5.

Figure 6:
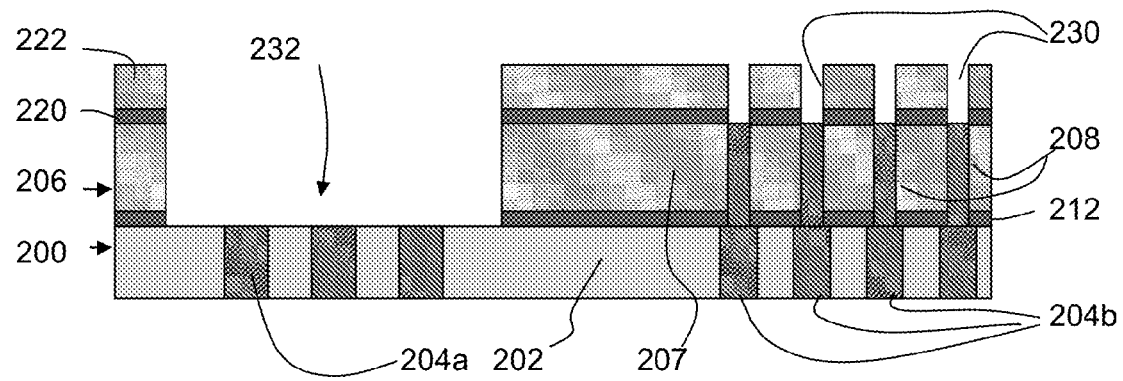

Deep bond pad holes are then patterned in the entire dielectric stack (two dielectric layers 207,222 and two etch stop layers 212,220) with a mask for defining the bond pad. This is the same "pad open" mask that is required to form the bond pad of the known structure, for example as shown in FIG. 2. This bond pad etching is shown in FIG. 6 and form a bond pad opening 232.

The final resist strip process etches through the bottom SiN layer 212 in the deep bond pad holes and the shallow via holes 230 simultaneously. However, alternative recipes may be used instead, e.g., where the bottom SiN layer in the shallow via holes is already partially or even fully etched during the shallow via patterning step of FIG. 5.

Figure 7:
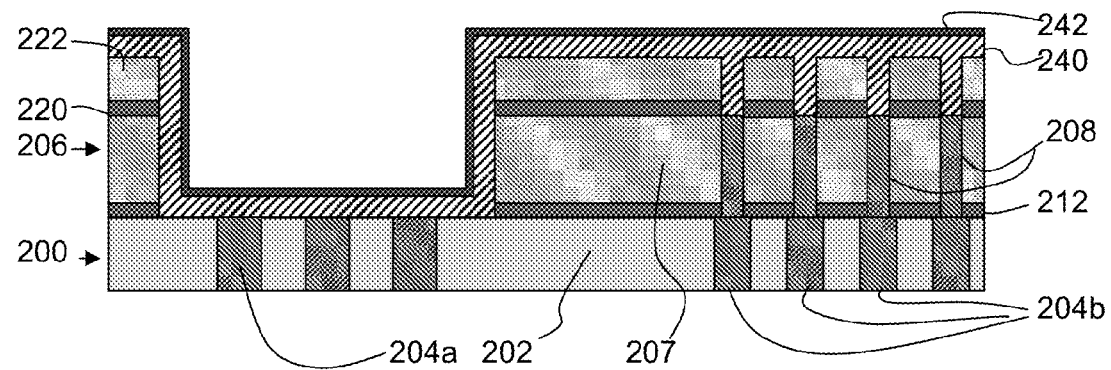

A diffusion barrier is then applied. This can be a modified design, consisting of a thicker than normal Tantalum nitride layer 240 and a regular Ta layer 242 as shown in FIG. 7. The thickness of the Tantalum nitride layer 240 should be tuned in such a way that it completely fills the shallow nanoelectrode holes 230, and that the lower part of residual seams or cusps end above the top of the top cap layer 222, so that they are removed in a later CMP step.

For a 90-nm CMOS node, typical dimensions are:
thickness of capping layer 222 of 150 nm;
width of the holes 230 of 130 nm;
thickness of the TaN layer 240 of 100-150 nm (measured at the surface before CMP);
thickness of the Ta layer of 2-5 nm.

Figure 8:
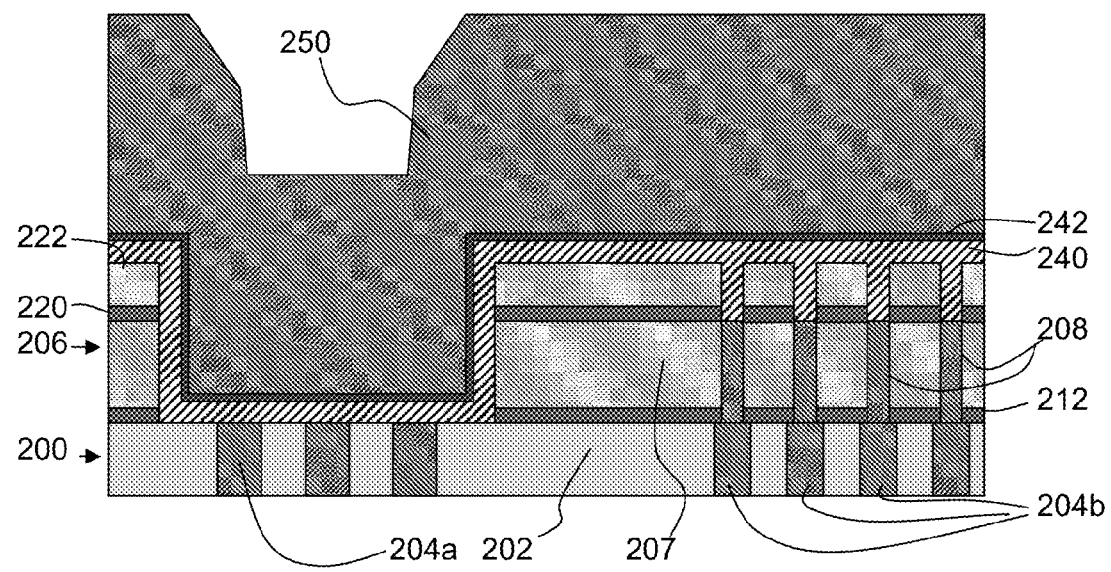

As shown in FIG. 8, a copper layer 250 is electroplated on the modified tantalum nitride/tantalum diffusion barrier in a standard way, for example starting with a copper seed layer. It should be thick enough to well overfill the deep bond pad holes. Subsequently an anneal/sintering process, for example a 400-430° C. forming gas anneal using a mixture of 10-20% hydrogen with nitrogen, is carried out to remedy plasma damage in the MOS transistors produced in the front-end processing stage.

Figure 9:
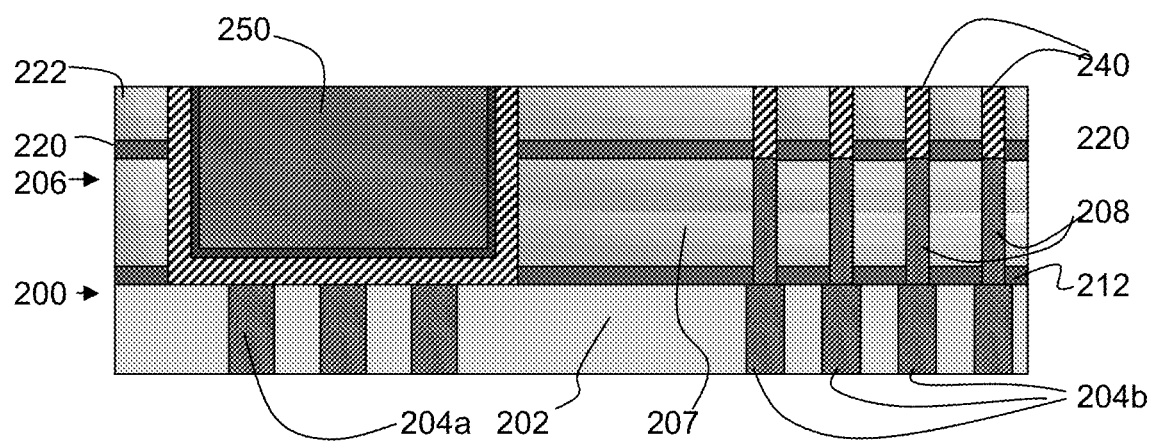

Finally, the wafer is planarized with a copper CMP step, resulting in the structure shown in FIG. 9. The tantalum nitride in the nanoelectrodes is planarized during the final diffusion barrier removal step of the copper CMP process module. This barrier removal step has to be tuned to yield flat and smooth tantalum nitride nanoelectrode surfaces with minimal recess.

Optionally, the copper bond pads can be protected against corrosion with a hydrophobic thiol-based self-assembled monolayer (SAM), e.g., Cu—S—$(CH_2)17$-$CH_3$, or by a corrosion inhibitor that can be deposited selectively on the exposed copper areas. Finally, the tantalum nitride nanoelectrodes can be bio-functionalized by first depositing a silane-based SAM on the Tantalum nitride surfaces, and then coupling biomolecules to this SAM.

Such silane-based SAMs have much better stability than thiol-based SAMs. Because the tantalum nitride nanoelectrode surfaces have much better corrosion resistance than copper, the resulting functionalized nanoelectrodes have superior overall stability compared to copper- or gold-based nanoelectrodes functionalized with intermediate thiol-based SAMs.

The biological probe molecules can easily be attached to the oxidised tantalum surface layer. Electrical connections can be made to the bond pads with aluminium bond wires, for example.

All materials, processing steps, and their order in the proposed process flow are available in a standard advanced CMOS process flow. The invention resides in the way they can be used surprisingly outside their regular ranges, especially the depth of the shallow nanoelectrode holes in combination with the thickness of the tantalum nitride layer in the diffusion barrier, but still within ranges that are well achievable with standard process equipment.

The combination of Ta and TaN is of particular interest to achieve prolonged device lifetimes despite electromigration issues. The structure also enables Ta to be in contact with copper in the bond pads to provide good copper adhesion, and enables TaN to be in contact with the underlying dielectric layer, again with good adhesion properties.

However, the invention can be applied to a structure having only Ta as the nanoelectrode material, instead of a Ta/TaN stack. In particular, the detection electrodes do not pass high current densities, and the biosensor device is not intended for continuous operation. As a result, electromigration issues are less relevant. As a result, the use of a thick layer of Ta only as the nanoelectrode material is possible, and indeed Ta only has been used in the past as a diffusion barrier in CMOS technology. The barrier may also be a three-layer stack in other examples.

The invention allows manufacturing the entire structure up to the final copper CMP, and optionally including the deposition of a copper corrosion inhibitor, in a standard CMOS fabrication plant.

The invention is applicable to biosensor chips, by which is meant a biosensor that is formed as an integrated circuit in semiconductor technology, for example in silicon semiconductor technology, and preferably in CMOS technology. A monolithically integrated biosensor chip has the property of very small dimensions thanks to the use of micro-processing technology, and may therefore have a large spatial resolution and a high signal-to-noise ratio particularly when the dimensions of the components of the biosensor chip approach or reach the order of magnitude of the dimensions of biomolecules.

The sensor can be used for detection of particles which play a significant role in biology or in biological or biochemical procedures, such as genes, DNA, RNA, proteins, enzymes, cells, bacteria, virus, etc.

The sensor is typically for sensing a fluidic sample. Such fluids may include liquids, gases, plasmas and, to some extent, solids, as well as mixtures thereof. Examples for fluidic samples are DNA containing fluids, blood, interstitial fluid in subcutaneous tissue, muscle or brain tissue, urine or other body fluids. For instance, the fluidic sample may be a biological substance. Such a substance may comprise proteins, polypeptides, nucleic acids, DNA strands, etc.

Various modifications will be apparent to those skilled in the art.

The invention claimed is:
1. A method of forming a biosensor chip, comprising:
forming semiconductor components in a semiconductor wafer;
forming filled electrically conductive connection regions in a dielectric layer overlying the semiconductor components, the filled electrically conductive connection regions making electrical contact to the semiconductor components, and comprising at least a bond pad connection region and a detection electrode connection region;

forming a first capping layer over the dielectric layer, and forming at least one filled electrically conductive connection via in the first capping layer making contact with the detection electrode connection region wherein no connection vias are formed over the at least one bond pad connection region;

forming a second capping layer over the first capping;

forming at least one via in the second capping layer, aligned with the at least one filled electrically conductive connection via in the first capping layer;

forming a bond pad opening in the second capping layer, over the bond pad connection region and extending down to the dielectric layer;

forming a diffusion barrier over the top of the structure and which completely fills the at least one via in the second capping layer;

providing a bond pad connection layer over the top of the structure and which fills the diffusion barrier-lined bond pad opening; and planarizing the structure down to the second capping layer.

2. A method as claimed in claim 1, wherein the same mask is used for forming the at least one filled electrically conductive connection via in the first capping layer and for forming the at least one via in the second capping layer.

3. A method as claimed in claim 1, wherein forming the first capping layer further comprises forming an etch stop layer beneath the first capping layer and forming the second capping layer further comprises forming an etch stop layer beneath the second capping layer.

4. A method as claimed in claim 1, wherein forming the diffusion barrier comprises forming a tantalum nitride layer which fills the at least one via in the second capping layer, and a tantalum layer over the tantalum nitride layer, wherein the tantalum nitride layer is thicker than the tantalum layer.

5. A method as claimed in claim 4, wherein the planarizing removes the bond pad connection layer and the tantalum layer from over the detection electrode connection region.

6. A method as claimed in claim 1, wherein the or each etch stop layer comprises silicon nitride, silicon carbide, or a combination of the two.

7. A method as claimed in claim 1, wherein the first and second capping layers comprise oxide layers.

8. A method as claimed in claim 1, wherein the second capping layer comprises a stack of silicon oxide and silicon nitride.

9. A method as claimed in claim 1, wherein the filled electrically conductive connection regions in the dielectric layer and the filled electrically conductive connection via in the first capping layer are each filled with copper.

10. A method as claimed in claim 1, wherein the second capping layer is thinner than the first capping layer, and the via formed in the second capping layer has a depth:width aspect ratio of less than 1.5.

11. A method as claimed in claim 1, wherein the planarizing comprising a copper chemical mechanical polishing process and which is used to remove the barrier material down to the surface of the second capping layer.

12. A biosensor chip, comprising:

semiconductor components formed in a semiconductor wafer;

filled electrically conductive connection regions in a dielectric layer overlying the semiconductor components, the filled electrically conductive connection regions making electrical contact to the semiconductor components, and comprising at least a bond pad connection region and a detection electrode connection region;

a first capping layer over the dielectric layer having at least one filled electrically conductive connection via in the first capping layer making contact with the detection electrode connection region;

a second capping layer over the first capping layer and having at least one via aligned with the at least one filled electrically conductive connection via in the first capping layer and a bond pad opening over the bond pad connection via and extending down to the dielectric layer;

wherein the bond pad opening is lined with a diffusion barrier comprising a tantalum nitride layer and a tantalum layer over the tantalum nitride layer and is filled over the diffusion barrier with a conductor, wherein the tantalum nitride layer is thicker than the tantalum layer, and wherein the at least one via of the second capping layer is completely filled with tantalum nitride.

13. A chip as claimed in claim 12, comprising an etch stop layer beneath the first and second capping layers.

14. A chip as claimed in claim 12, wherein the second capping layer is thinner than the first capping layer, and the via formed in the second capping layer has a depth:width aspect ratio of less than 1.5.

15. A chip as claimed in claim 12, wherein the filled electrically conductive connection regions in the dielectric layer and the filled electrically conductive connection via in the first capping layer are each filled with copper, and the conductor filling the bond pad opening is copper.

* * * * *